(12) United States Patent
Hao

(10) Patent No.: US 7,932,380 B2
(45) Date of Patent: Apr. 26, 2011

(54) PROCESS FOR THE PREPARATION OF SUCRALOSE

(75) Inventor: Xiangyang Hao, Shanghai (CN)

(73) Assignee: Wanhe International (Group) Co. Ltd., Wilmington, DE (US)

( * ) Notice: Subject to any disclaimer, the term of this patent is extended or adjusted under 35 U.S.C. 154(b) by 520 days.

(21) Appl. No.: 12/043,554

(22) Filed: Mar. 6, 2008

(65) Prior Publication Data

US 2009/0227783 A1    Sep. 10, 2009

(51) Int. Cl.
*C07H 1/00* (2006.01)
(52) U.S. Cl. ........................................ 536/124
(58) Field of Classification Search ............. 536/124
See application file for complete search history.

(56) References Cited

U.S. PATENT DOCUMENTS

| | | | |
|---|---|---|---|
| 4,380,476 A | 4/1983 | Mufti | |
| 4,889,928 A | 12/1989 | Simpson | |
| 4,950,746 A | 8/1990 | Navia | |
| 4,977,254 A * | 12/1990 | Homer et al. | 536/124 |
| 4,980,463 A * | 12/1990 | Walkup et al. | 536/124 |
| 5,023,329 A | 6/1991 | Neiditch et al. | |
| 5,449,772 A * | 9/1995 | Sankey | 536/115 |

FOREIGN PATENT DOCUMENTS

| | | |
|---|---|---|
| GB | 2079749 A | 1/1982 |
| GB | 2181374 A | 4/1987 |

* cited by examiner

*Primary Examiner* — Shaojia Anna Jiang
*Assistant Examiner* — Ganapathy Krishnan
(74) *Attorney, Agent, or Firm* — WPAT, P.C.; Anthony King

(57) ABSTRACT

A process for the preparation of a sucralose which comprises the steps of: reacting a sucrose with a chlorinating reagent in a non-proton type polar solvent to form chlorinated sucrose (4,6,1',6'-tertchloro-4,6,1',6'-tertdeoxylgalactosucrose); reacting the chlorinated sucrose and a carboxylate salt to form sucralose-6-acetate in a dissolvent; and finally de-acylating the sucralose-6-acetate in sodium methoxide/methanol system and then the desired product sucralose is thereby produced. The present invention is generally related to the industrial production of sucralose with the advantages of mild reaction conditions, high yield rate, and brief operation.

9 Claims, No Drawings

PROCESS FOR THE PREPARATION OF SUCRALOSE

FIELD OF THE INVENTION

The invention generally related to the chemical synthesis field and more particularly to an improvement method for the preparation of sucralose.

BACKGROUND OF THE INVENTION

The artificial sweetener 4,1',6'-trichloro-4,1',6'-trideoxy-galactosucrose (sucralose) is derived from sucrose by replacing the hydroxyls in the 4,1', and 6' position with chlorine. It is 600 times sweeter than cane sugar, and does not participate in human metabolism, and is one of particular interest for use as low calorie sweetener to replace saccharin in various products, including foods, candy, beverages and orally received medicines such as cough drops. Sucralose has the characteristics of high safety and particularly it exhibits the stability in acid aqueous solution. Owing to these advantages, the sucralose is one of the most popular and stronger sweeteners in the market.

However, according to the molecular structure of the sucralose, a major problem of synthesis sucralose is in the field of how only direct the chlorine atoms to the desired positions, if the competition from other reactivity of the hydroxyls came. The synthesis is further complicated by the fact that the primary hydroxyl in the 6 position is un-substituted in the final product. Until now, a number of different synthetic routes for the preparation of sucralose have been developed that the main synthesis methods are omni-group protection method and mono-group protection method at presence, of which the former is not widely used owing to its low yield, complicated operation, high cost and etc.

Considerable work has been carried out to study the mono-group protection method, all of which involve chlorination of the sucrose in the 4,1', and 6' position, such as U.S. Pat. Nos. 4,889,928, 5,449,772, 5,023,329, 4,950,746, which focuses on description the synthesis of sugar-6-acetate, while limited information given on part of chlorinated synthesis. Besides, the U.S. Pat. No. 4,380,476 and GB2079749 disclose that sucralose is acylated at the 6-position and the 4,1' and 6' positions and then are chlorinated in the presence of unprotected hydroxy groups at the 2,3,3' and 4' positions. The GB2181374A also disclosed the method of using thionyl chloride in pyridine with triaryphosphine oxide to synthesis the sucrose, but the question is that the triaryphosphine oxide is troublesome to remove and recycle. What is more, not only the pyridine is toxic and odorous, but also the reaction condition gives more amounts of black insoluble by-product, therefore, it is difficult to work up.

In view of the shortcomings of the prior art, the inventor of the present invention based on years of experience to conduct extensive researches and experiments, and finally developed an advanced method for preparation of surcalose to overcome the shortcomings of the prior art.

SUMMARY OF THE INVENTION

The object of the present invention is to find out an improvement method for the preparation of sucralose with high purity, low cost, high yield, brief process in mild conditions and has the stable industrial production characters.

According to the objective of the present invention, a process for the preparation of a sucralose has been presented where comprises the steps of reacting a sucrose with a chlorinating reagent in a aprotic polar solvent to form chlorinated sucrose (4,6,1', 6' tetrachloro-4,6,1', 6' tetradeoxylgalactosurose); reacting the chlorinated sucrose with a carboxylate salt in a dissolvent to form sucralose-6-acetate; and finally de-acylating the sucralose-6-acetate in a sodium methoxide/methanol system and then the desired product sucralose is produced.

To make it easier for our examiner to understand the objective of the invention, its innovative features and performance, a detailed description and technical characteristics of the present invention are described as following.

BRIEF DESCRIPTION OF THE DRAWINGS

None.

DETAILED DESCRIPTION OF THE PREFERRED EMBODIMENTS

The forgoing and other objects, features and advantages of the present invention will be better understood from the following detailed description taken with the accompanying drawing, and the same referring numerals are used for the same components in accordance with the present invention.

According to the objective of the present invention, a process for the preparation of a sucralose has been presented which comprises the steps of:
(a) reacting a sucrose with a chlorinating reagent in a aprotic polar solvent to form chlorinated sucrose (4,6,1',6' tetrachloro-4,6,1',6' tetradeoxylgalactosurose).
(b) reacting the chlorinated sucrose (4,6,1',6' tetrachloro-4,6,1',6'-tetradeoxylgalactosurose) with a carboxylate salt in a dissolvent to form sucralose-6-acetate.
(c) de-acylating the sucralose-6-acetate in a sodium methoxide/methanol system and then the desired product sucralose is produced.

In the above stated improvement method of preparation of sucralose, the chlorinating reagent is thionyl chloride, phosgene, solid phosgene, phosphorus trichloride, phosphorus oxychloride, or phosphorus pentachloride.

In the above stated improvement method of preparation of sucralose, the chlorinating reagent is added in an amount of at least 7 mole equivalents of the sucrose.

In the above stated improvement method of preparation of sucralose, the aprotic polar solvent is N, N-dimethyl formamide, dimethyl sulfoxide, or hexamethyl phosphoramide.

In the above stated improvement method of preparation of sucralose, the step of reacting the sucrose with the chlorinating reagent is carried out at a temperature range from −15° to 120°.

In the above stated improvement method of preparation of sucralose, the carboxylate is sodium acetate, potassium acetate, sodium benzoate, or potassium benzoate.

In the above stated improvement method of preparation of sucralose, the dissolvent is N, N-dimethyl formamide, dimethyl sulfoxide, or hexamethyl phosphoramide.

In the above stated improvement method of preparation of sucralose, the amount of carboxylate is added in an amount of range from 1 mole equivalent to 5 mole equivalents of the chlorinated sucrose.

In the above stated improvement method of preparation of sucralose, the step of reacting the chlorinated sucrose with the carboxylate salt is carried out at a temperature range from 30° to 100°.

In the above stated improvement method of preparation of sucralose, the step of de-acylating the sucralose-6-acetate is carried out at a temperature range from 30° to 50°.

The synthesis process from sucrose to high purity sucralose goes as follows:

1. Synthesis of 4,6,1', 6'-tetrachloro-4,6,1', 6'-tetradeoxylgalactosurose

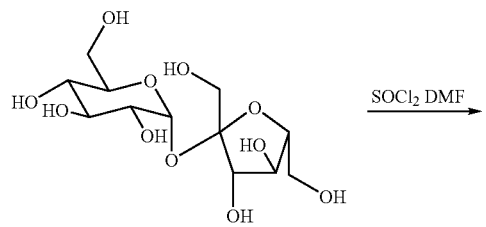

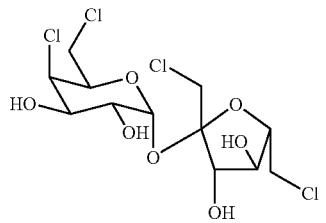

The chlorination process can be straightforwardly controlled that the efficiency of sugar transformation is over 94%. It can be completed in 6-10 hours without charring. The reaction was conducted at the temperature range of less than 120°. The higher temperature it is, the more impurities are come out.

2. Synthesis of Sucralose-6-acetate

In a aprotic polar solvent, the chlorinated sucrose (4,6,1 ', 6'-tetrachloro-4,6,1 ', 6'-tetradeoxylgalactosurose) can react with the carboxylate salt with mild reaction conditions and brief process to form the sucralose-6-acetate.The reaction time is about 6-8 hours.

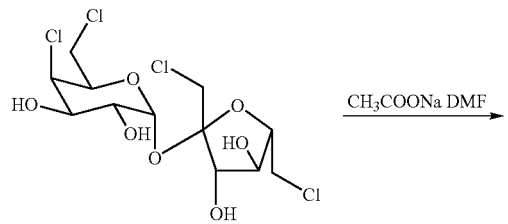

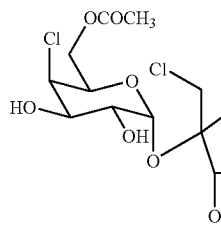

3. Synthesis of Sucralose

The de-acetyling of sucralose-6-acetate have good yield in a methanol solution with catalyst of sodium methoxide. The reaction temperature range is controlled from 30° to 50°.

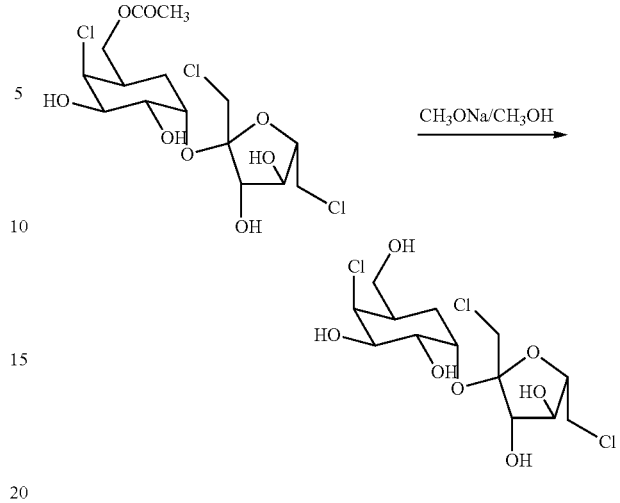

According to the above synthesis process, the yield of sucralose can be 36% or more than the cane sugar on weight basis. To the best of applicants' knowledge, the preparation of sucralose in the invention has no literature precedent. Compared with the reported sucralose production process, the invention has features of good yield, good purity, mild reaction condition, cost effective and economically feasible, safe, and industrially feasible.

EXAMPLE 1

Preparation of 4,6,1', 6'-tetrachloro-4,6,1', 6'-tetradeoxylgalactosurose

A 500mL, four-neck, round-bottom flask, equipped with mechanical stirrer, thermometer, addition funnel, and reflux condenser topped with an argon inlet, was charged with 25g of sucrose and 240g of DMF. This solution was cooled down to −10°, and then added dropwise over 1h with 78g of thionyl chloride. During the addition, the precipitate was formed. The slurry became easier to stir as the temperature of the reaction mixture increased. After that, the solution was heated to 90° over a period of 2h, heated to 110° over another period of 2h, and then held at this temperature for 1h. Next, the reaction mixture was cooled down to 0° again, stirred at this temperature for 15min and then added 100mL ice cold 4N NaOH with vigorous stirring that the pH value was about 9 after the addition. Then, the reaction mixture keeps vigorous stirring and then adds certain amount of glacial acetic acid to adjust the pH value to 7. Afterward, around 300mL ethyl acetate was added and the organic layer was separated. The aqueous layer was further extracted with ethyl acetate (2×200mL). The combined organic layer was washed with water and removed under vacuum condition. Consequently, the residue was dried in high-vacuum condition to give 25.4g crude 4,6,1', 6'-tetrachloro -4,6,1 ', 6' tertradeoxylgalactosucrose.

EXAMPLE 2

Preparation of 4,6,1', 6'-tetrachloro-4,6,1', 6'-tetradeoxylgalactosurose 144g of Dimethyl formamide(DMF) was added dropwise 78g of thionyl chloride at −10° with vigorously stirring over a period of 1h, and the precipitate was observed. The reaction mixture was held at this temperature for 30min, then added 25g of sucrose which dissolving in 96g of DMF. After completely the addition, the reaction mixture was then heated to 90° over a period of 2h, heated to 110° over another period of 2h, and held at this temperature for 1h. Next, the reaction mixture was cooled down to 0°, stirred at this temperature for 15min and then added 100 mL ice cold 4N NaOH with vigorous stirring that the pH value was about 9 after the addition. Then, the reaction mixture was vigorously stirred to adjust pH value to 7 by adding certain amount of glacial acetic acid. Afterward, around 300mL ethyl acetate was added and the organic layer was separated. The aqueous layer was further extracted with ethyl acetate (2×200mL). The combined organic layers was washed with water and removed under vacuum condition. The residue was dried in high-vacuum condition to give 25.8g crude 4,6,1', 6' tetrachloro-4,6,1 ', 6'-tetradeoxylgalactosurose.

EXAMPLE 3

Preparation of Sucralose-6-acetate

The solution of 25.8g of 4,6,1', 6' tetrachloro-4,6,1', 6'-tetradeoxylgalactosurose and 80g of DMF was added by 6g of anhydrous sodium acetate, and stirred at 50° for 6h under nitrogen condition. The reaction mixture was then added 30mL water, and then extracted by 300mL ethyl acetate. The organic layer was separated afterward. The aqueous layer was further extracted with ethyl acetate (2×200mL). Afterward, each extracted organic solvent was combined together and then treated with about 3g of activated carbon for about 30min at ambient temperature. The slurry was filtered and the cake washed with ethyl acetate. The resulting filtrate was evaporated and concentrated under vacuum condition. The residue was dried in high-vacuum condition and to give 21g crude sucralose-6-acetate. The crude was re-crystallized in 30g water to afford 15.8g sucralose-6-acetate.

EXAMPLE 4

Preparation of Sucralose-6-acetate

The solution of 25.8g of 4,6,1',6' tetrachloro-4,6,1',6'tetradeoxylgalactosurose and 80g of DMF was added by 6g of sodium benzoate, and stirred at 50° for 6h under nitrogen condition. The reaction mixture was then added 30mL water, and then extracted with 300mL ethyl acetate. Afterward, each extracted organic solvent was combined together and then treated with about 3g of activated carbon for about 30min at ambient temperature. The slurry was filtered and the cake washed with ethyl acetate. The resulting filtrate was evaporated and concentrated under vacuum condition. The residue was dried in high-vacuum condition and to give 21g crude sucralose-6-acetate. The crude was recrystallized from 30g of water to afford 15g of pure sucralose-6-acetate.

EXAMPLE 5

Preparation of Sucralose

To a solution of 15.8g of sucralose-6-acetate and 120g of methanol was added by 0.15g of sodium methoxide. The reaction mixture was stirred at 30° for 4 hours. Then, the reaction mixture was neutralized to pH7, filtered and then the filtrate was decolored with activated carbon and concentrated under vacuum condition to afford the crude sucralose. The crude was recrystallized from water to afford 9.5g of pure sucralose with over 99% purity.

While the invention has been described by way of examples, it is to be understood that the invention is not limited thereto. To the contrary, it is intended to cover various modifications and similar arrangements and procedures, and the scope of the appended claims therefore should be accorded the broadest interpretation so as to encompass all such modifications and similar arrangements and procedures. In summation of the description above, the present invention is novel and useful and definite enhances the performance over the conventional methods and further complies with the patent application requirements and is submitted to the Patent and Trademark Office for review and granting of the commensurate patent rights.

What is claimed is:

1. A process for the preparation of sucralose, comprising the steps of:
   (a) reacting sucrose with a chlorinating reagent in an aprotic polar solvent to form chlorinated sucrose (4,6,1',6'-tetrachloro-4,6,1',6'-tetradeoxylgalactosucrose);
   (b) reacting said chlorinated sucrose with a carboxylate salt in the aprotic polar solvent to form sucralose-6-acetate or sucralose-6-benzoate; and
   (c) de-acylating said sucralose-6-acetate or said sucralose-6-benzoate in a methanol solution with sodium methoxide and then the desired product sucralose is thereby produced.

2. The process of claim 1, wherein said chlorinating reagent is thionyl chloride, phosgene, solid phosgene, phosphorus trichloride, phosphorus oxychloride, or phosphorus pentachloride.

3. The process of claim 1, wherein said chlorinating reagent is added in an amount of at least 7 mole equivalents of said sucrose.

4. The process of claim 1, wherein the aprotic polar solvent is N, N-dimethyl formamide, dimethyl sulfoxide, or hexamethyl phosphoramide.

5. The process of claim 1, wherein the step of reacting the sucrose with the chlorinating reagent is carried out at a temperature range from −15° to 120°.

6. The process of claim 1, wherein said carboxylate salt is sodium acetate, potassium acetate, sodium benzoate, or potassium benzoate.

7. The process of claim 1, wherein said carboxylate salt is added in an amount ranging from 1 mole equivalent to 5 mole equivalents of said chlorinated sucrose.

8. The process of claim 1, wherein the step of reacting the chlorinated sucrose (4,6,1',6'-tetrachloro-4,6,1',6'-tetradeoxyl galactosucrose) with the carboxylate salt is carried out at a temperature range from 30° to 100°.

9. The process of claim 1, wherein the step of de-acylating the sucralose-6-acetate is carried out at a temperature range from 30° to 50°.

* * * * *